US012523215B2

(12) United States Patent
Bartsch

(10) Patent No.: US 12,523,215 B2

(45) Date of Patent: Jan. 13, 2026

(54) PIEZOELECTRIC DISPLACEMENT UNIT FOR A MEDICAL HOSE PUMP AND MEDICAL HOSE PUMP

(71) Applicant: B. Braun Melsungen AG, Melsungen (DE)

(72) Inventor: Stefan Bartsch, Neuenstein (DE)

(73) Assignee: B. Braun Melsungen AG, Melsungen (DE)

( * ) Notice: Subject to any disclaimer, the term of this patent is extended or adjusted under 35 U.S.C. 154(b) by 287 days.

(21) Appl. No.: 18/356,656

(22) Filed: Jul. 21, 2023

(65) Prior Publication Data

US 2024/0024570 A1 Jan. 25, 2024

(30) Foreign Application Priority Data

Jul. 21, 2022 (DE) ..................... 10 2022 118 250.9

(51) Int. Cl.
*F04B 43/12* (2006.01)
*A61M 5/142* (2006.01)
*A61M 60/284* (2021.01)

(52) U.S. Cl.
CPC ..... *F04B 43/1223* (2013.01); *A61M 5/14228* (2013.01); *A61M 60/284* (2021.01)

(58) Field of Classification Search
CPC ............. A61M 5/14228; A61M 60/284; F04B 43/1223
See application file for complete search history.

(56) References Cited

U.S. PATENT DOCUMENTS

| | | | | |
|---|---|---|---|---|
| 5,954,485 | A | 9/1999 | Johnson et al. | |
| 6,150,750 | A | 11/2000 | Burov et al. | |
| 10,928,236 | B2 | 2/2021 | Adler et al. | |
| 11,885,323 | B2 * | 1/2024 | Mar | F04B 43/0733 |
| 2003/0085633 | A1 | 5/2003 | Marth | |
| 2008/0038128 | A1 | 2/2008 | Haar | |
| 2011/0105981 | A1 | 5/2011 | Wagner et al. | |
| 2016/0245271 | A1 | 8/2016 | Schaefer et al. | |
| 2025/0207578 | A1 * | 6/2025 | Nikolovski | A61M 5/14228 |

FOREIGN PATENT DOCUMENTS

| | | | | |
|---|---|---|---|---|
| CN | 108348679 | A * | 7/2018 | F04B 43/09 |
| CN | 108626102 | A * | 10/2018 | F04B 43/12 |
| DE | 10118086 | A1 | 7/2002 | |
| DE | 102005046516 | A1 | 4/2007 | |
| DE | 102007034125 | A1 * | 1/2009 | F04B 43/082 |
| DE | 202009014073 | U1 | 4/2010 | |
| DE | 102012012229 | A1 | 12/2013 | |
| DE | 102012012839 | A1 | 12/2013 | |

(Continued)

OTHER PUBLICATIONS

English Machine Translation of CN-108348679-A (Year: 2018).*

(Continued)

*Primary Examiner* — Nathan C Zollinger
(74) *Attorney, Agent, or Firm* — Christopher A. Rothe; CM Law

(57) ABSTRACT

A displacement unit for a medical hose pump and a medical hose pump having such a displacement unit. The displacement unit has linearly movable displacers that can be actuated by a drive device of the displacement unit transversely to a conveying direction against a hose.

14 Claims, 5 Drawing Sheets

(56) References Cited

FOREIGN PATENT DOCUMENTS

| | | | | | |
|---|---|---|---|---|---|
| DE | 102013108948 | A1 | * | 2/2015 | ............. H02N 2/021 |
| DE | 102015216050 | A1 | | 2/2017 | |
| DE | 102020113267 | A1 | | 11/2021 | |
| EP | 0484717 | B1 | | 9/1994 | |
| EP | 1834658 | B1 | | 12/2009 | |
| EP | 2209203 | A3 | | 11/2010 | |
| EP | 2316502 | A1 | | 5/2011 | |
| EP | 3061473 | B1 | | 5/2019 | |
| EP | 4575226 | A1 | * | 6/2025 | .......... F04B 43/0081 |
| JP | H024382 | A1 | * | 1/1990 | |
| WO | 9831935 | A1 | | 7/1998 | |
| WO | WO-2013041703 | A1 | * | 3/2013 | .......... F04B 43/1223 |
| WO | WO-2020166560 | A1 | * | 8/2020 | .............. F04B 43/12 |

OTHER PUBLICATIONS

English Machine Translation of DE-102007034125-A1 (Year: 2009).*
English Machine Translation of JP-H024382-A1 (Year: 1990).*
English Machine Translation of CN-108626102-A (Year: 2018).*
Search Report received in German Application No. 10 2022 118 250.9 dated Mar. 29, 2023, with translation, 9 pages.
Search Report received in European Application No. 23186779.7-1004 dated Oct. 2, 2023, with translation, 10 pages.
Office Action received in European Application No. 23 186 779.7-1009 dated Nov. 11, 2025, with translation, 9 pages.

* cited by examiner

PIEZOELECTRIC DISPLACEMENT UNIT FOR A MEDICAL HOSE PUMP AND MEDICAL HOSE PUMP

CROSS-REFERENCE TO RELATED APPLICATION(S)

This application claims priority under 35 U.S.C. § 119 to German Application No. 10 2022 118 250.9, filed on Jul. 21, 2022, the contents of which is incorporated by reference herein in its entirety.

FIELD

The present disclosure relates to a peristaltic displacement unit for a medical hose pump, and to a medical hose pump comprising the displacement unit.

BACKGROUND

The dosage of medical agents or the delivery of blood in extracorporeal blood treatment can be performed by a hose pump. One principle of operation of such a hose pump is generally to impose a peristaltic movement on a hose through which a fluid is passed via a displacement unit of the hose pump, whereby the fluid is conveyed from an active substance container to an access point on the patient.

A hose pump of radial design is disclosed in patent EP 3 061 473 B1 of the Applicant. The hose pump shown for extracorporeal blood treatment has a motorized rotary drive with a rotor, on which squeezing elements are provided radially on the outside, which repeatedly slide or roll on a hose portion, which is supported fixedly to the housing and has an arc shape, in a longitudinal direction of the hose during rotation. In this way, the hose portion undergoes a periodic, peristaltic cross-sectional constriction so that the blood is conveyed in the direction of rotation of the rotor.

A hose pump of linear design is shown in patent EP 0 484 717 B1 of the Applicant. It has a receptacle for a hose, through which fluid is conveyed, and a displacement unit with a plurality of slide-like displacers, which are arranged side by side along the receptacle and are guided linearly movable transversely to the receptacle in a shaft-like housing portion. End portions of the sliders opposite the receptacle are actuated by a rotating eccentric shaft mounted for rotation thereon, wherein an eccentric element is associated with each slider and adjacent eccentric elements have an angular offset in the direction of rotation of the eccentric shaft. The rotation of the eccentric shaft thus causes the linear, time-delayed actuation of the slides and consequently the squeezing of the hose according to a peristaltic pattern, which in turn results in the conveyance of fluid. The shaft is mounted to be displaceable in the direction in which the slide valves are actuated. Any tolerances of the hose or of the hose pump can be compensated by an adjustable spring, which loads the displacement unit in the direction of actuation of the slide valves.

A hose pump is known from the Applicant's product range under the federally registered trademark INFUSOMAT® COMPACT$^{PLUS}$. It, too, has a displacement unit with linearly movable slides. End portions of the slides have a U-shaped coupling recess in which an eccentric shaft driven by a stepper motor engages. The linear guidance of the sliders causes the sliders to move back and forth in a linear motion when the eccentric shaft rotates. A position of the eccentric shaft is monitored by a light barrier with an encoder disk so that a control unit of the hose pump can be used, for example, to regulate a volume flow. The stepper motor and the eccentric shaft driven by it are pivotably mounted on a housing of the hose pump in such a way that the eccentric shaft is pressed against the displacers by an adjustable spring and loads it towards the hose. In this way, any tolerances of the hose or hose pump can also be compensated for by the adjustable spring.

With the linear design described above, in a disadvantageous way, a comparatively high number of components is required to effect the peristaltic movement of the hose on the one hand and to adjust the active engagement of the sliders with the hose on the other hand. Such a high number of components is associated with high costs for the development and design of the hose pump, a high effort to maintain tolerances and possible wear between the moving components. In addition, the displacement unit requires a large installation space due to the large number of components.

SUMMARY

The object of the present disclosure is to provide a displacement unit of linear design for a medical hose pump which reduces or eliminates disadvantages of the prior art and which, in particular, is simplified with respect to the device technology of the prior art. Furthermore, it is the object of the disclosure to provide a corresponding medical hose pump of linear design.

The object is solved by a displacement unit for a medical hose pump, in particular a hose pump which is an infusion device or an infusion pump or which is for medical dosage or for extracorporeal blood treatment, with linearly movable actuatable displacers (e.g. plungers), which are actuatable with a predetermined sequence (i.e. with a time delay, in particular in wave-like succession) by a drive device of the displacement unit for generating a peristaltic movement of a hose transversely to the hose (i.e. transversely to a longitudinal direction of the hose, in particular perpendicularly thereto) and against the hose in order to squeeze the hose. The drive device has linear motors, each of which is coupled to one of the displacers and at least one (preferably all) of which is a piezoelectric linear motor.

In other words, a displacement unit, also called a peristaltic unit, is provided for a medical hose pump, for example a metering pump or a dialysis pump. The displacement unit has a plurality (at least two, preferably four to sixteen, further preferably six to twelve) of linearly movable actuatable displacers which are or can be brought into contact with the fluid-carrying or blood-carrying hose of the hose pump and can be pressed against it, whereby a peristaltic movement in the sense of a progressive cross-sectional constriction is imparted to the hose. For this purpose, the displacers are actuatable transversely against the hose by a drive device of the displacement unit in a, in particular, predetermined sequence. According to the disclosure, the drive device has piezoelectric linear motors, each of which is coupled to one of the linearly movable displacers. The term linear motor is defined in this document such that the linear movement of the displacer effected by it is generated without a rotating shaft. The displacers are in particular passive components or plungers which are mechanically, in particular purely mechanically, coupled to the respective drive devices.

In this way, a displacement unit with simplified device technology is created, since the displacers are driven directly in their linear actuation direction by the linear motor and there is no need to convert a rotary drive movement into the desired linear movement of the displacers. This means that the components required for such a conversion can be dispensed with. Compared to the examples according to the prior art described in the introduction, this means in concrete terms that a stepper motor as well as an eccentric shaft or another corresponding gear for converting the rotational movement into the linear movement are superfluous. This reduction in the number of components already considerably reduces the installation space required by the displacement unit. As a result, there is also no need to support the eccentric shaft/gearbox or for coupling points or frictional connections between the eccentric shaft/gearbox and the displacers, which reduces wear. Due to the reduction in the number of components, the effort required to maintain tolerances is also reduced. In addition, piezoelectric linear motors are particularly compact, exhibit very low wear and can be controlled and/or regulated very well in terms of stroke, stroke speed and stroke force.

In a preferred further development, the respective displacer is coupled to more than one piezoelectric linear motor. These linear motors can be arranged on one side of the displacer parallel or in series to each other (with respect to a direction of movement of the displacer) and/or can be distributed on several sides of the displacer (in particular on opposite sides). In this way, an actuating force can be increased and a transmission of force to the displacer can be balanced. This reduces the risk of the displacer tilting, which makes it possible to reduce the effort required to support it.

In a preferred further development, a respective stroke, a respective stroke speed and/or a respective force of the linear motors, in particular a respective chronological sequence of the stroke or the force, is controllable or regulatable. Compared with the examples of the prior art described at the beginning, this eliminates the need for a complex mechanism for adjusting the preload of the displacer applied to the hose. The adjustment can thus be made by directly driving the linear motors instead of the conventional mechanically induced preload. This results in considerable savings in terms of components and installation space, which means that the displacement unit, and thus of course the hose pump containing it, can be made even smaller.

Preferably, the linear motors are each arranged laterally to the displacers with respect to a direction of movement of the displacers. This allows a considerable reduction in installation space, particularly in the direction of movement of the displacers.

Particularly preferably, the displacers each have at least one side edge, which is configured for friction fit and/or form fit with at least one actuator element, in particular an amorphous bending actuator, of the linear motors, wherein the side edge is in particular flat. This makes it possible to arrange the displacers and the associated linear motors particularly close to each other in the longitudinal direction of the hose, so that an installation space is further reduced and a particularly uniform peristaltic movement can be generated in the hose. Preferably, the displacers are disk-like plungers with their flat sides facing each other.

In a preferred further development, the displacement unit has a carrying structure or a housing structure in or on which the displacers are mounted linearly moveable and/or stators of the linear motors are fixed. The carrying or housing structure enables modular and therefore simple assembly of the displacement unit in the hose pump. Preferably, at least one lateral rim of the displacers, in particular adjacent to the lateral edge, is configured as at least one guide rail, which is guided longitudinally movable in/on the carrying structure. This means that only one (or if applicable two) rim and the associated edge have to be reworked and production costs can be reduced.

In a preferred further development, the housing or carrying structure has connection interfaces that are configured in such a way that the displacement unit is connectable to the medical hose pump in a determined manner in all degrees of freedom.

Preferably, the carrying structure or the housing structure has one or more shafts in which the displacers are mounted in a linearly moveable manner. They can be mounted, for example, via a respective plain bearing or a plain bearing arrangement.

In one further development, for height guidance or mounting of the displacers in the shaft, the shaft has at least one guide rim or guide surface on which the displacers are mounted in a linearly moveable manner. Preferably, two opposite guide rims or surfaces are provided between which the displacers are arranged and on which they are mounted in a linearly moveable manner.

In one further development, the shaft has guide lamellae or webs which extend into the shaft from the at least one guide rim/surface, preferably from both. The displacers (e.g. on one or both sides of the guide rail) are guided laterally in the shaft via the guide lamellas or webs and held at a distance so that their independent, interference-free actuation is ensured.

A medical hose pump, which in particular is an infusion device or an infusion pump or is for medical dosage or for extracorporeal blood treatment, has a housing with an externally accessible passage recess which can be spanned by a fluid-carrying or blood-carrying hose or into which the hose can be inserted. Preferably, diametrically arranged, externally accessible receptacles are formed on the housing at the side of the passage recess, into each of which a coupling portion of a fluid-carrying or blood-carrying hose can be received and in particular can be held in a form-fitting manner. A peristaltic displacement unit is accommodated in the housing, which is configured according to at least one aspect of the previous description and whose displacers can be brought into operative engagement with the hose through the passage recess or in the region of the passage recess in order to generate the peristaltic movement of the hose.

As already described above, the displacers of the displacement unit installed in the hose pump are actuated by linear motors, which results in the advantages of the displacement unit already mentioned and referred to here. As a result, the hose pump is also simplified in terms of device technology, requires less installation space, exhibits less wear and tear, and the effort required to maintain internal tolerances is reduced.

In order to safely separate a medical treatment space or application space from the machine interior housing space of the hose pump, in a further development the passage recess is spanned by a membrane, against which the displacers are effective on the inside.

BRIEF DESCRIPTION OF THE DRAWINGS

The disclosure is explained in more detail below with reference to an exemplary, non-limiting embodiment shown in the figures.

DESCRIPTION

Figure 1:
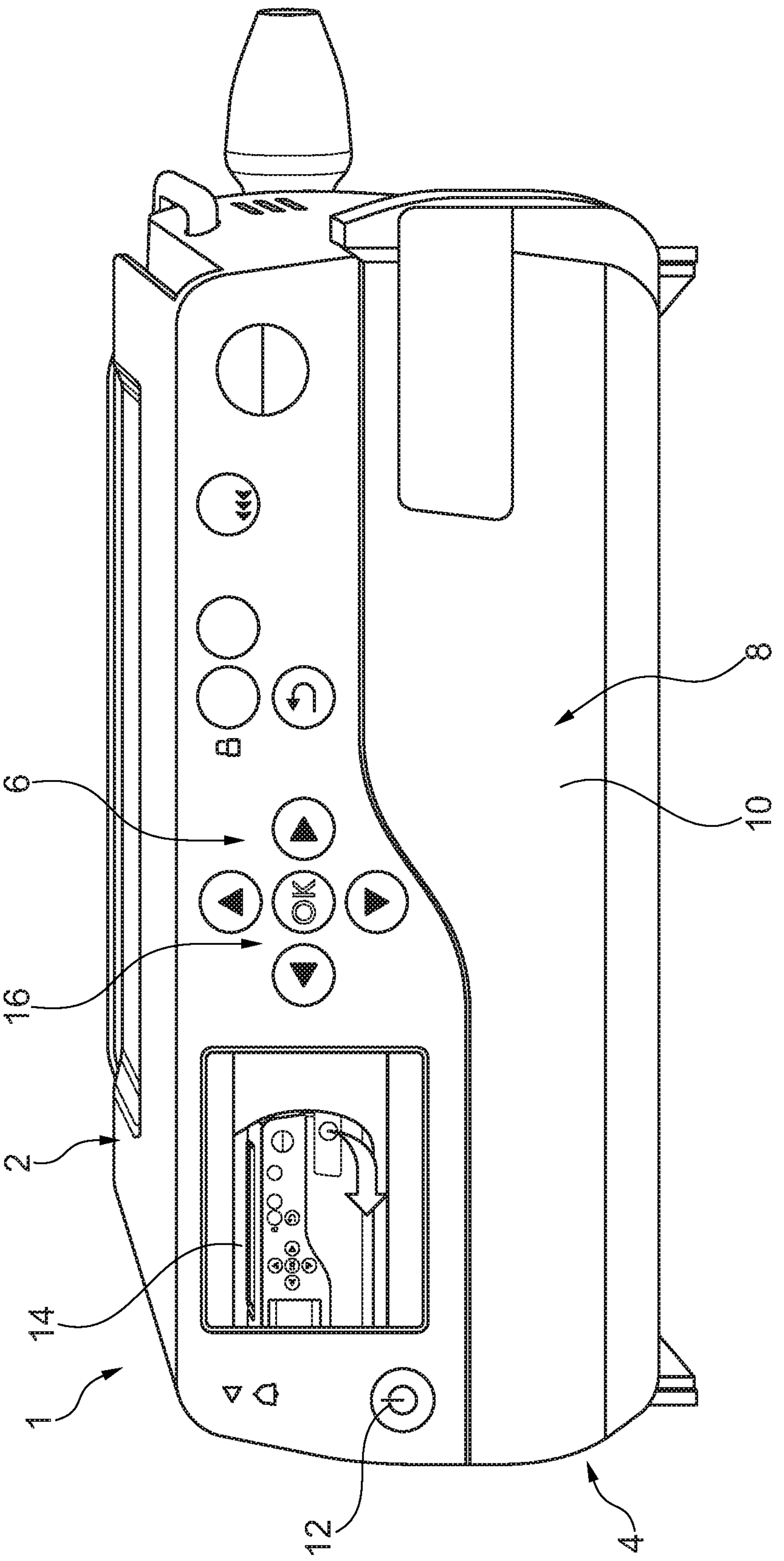
FIG. 1 shows a medical hose pump according to a configuration example in a front view.

FIG. 1 shows a front view of a medical hose pump 1 configured as an infusion device. The infusion device or hose pump 1 has an essentially cuboid housing 2 with a front side 4, which is essentially divided into an upper operator panel 6 and a lower, lockable hose compartment 8. The latter is covered by a hinged hose compartment lid 10.

The operator panel 6 has a plurality of buttons for operating the infusion device 1 and includes, among other things, an on/off button 12 a display 14 for displaying selected operating parameters, current operating variables, and an operating menu, a button arrangement 16 for navigating the operating menu and changing operating parameters, and other buttons for operation.

Figure 2:
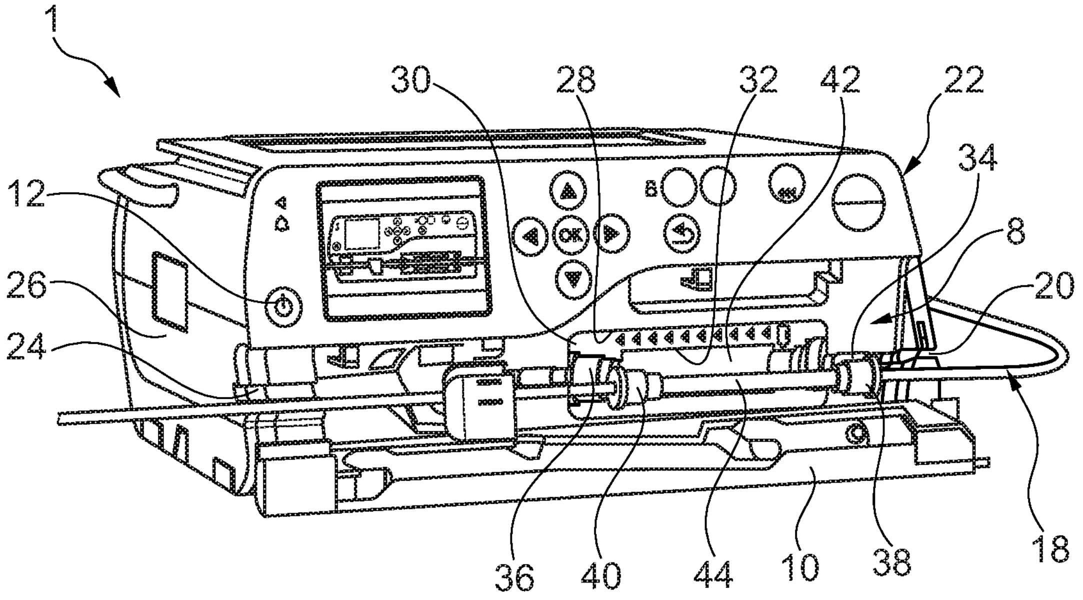
FIG. 2 shows the hose pump according to FIG. 1 in a perspective view from the front.

FIG. 2 shows the infusion device 1 according to FIG. 1 in a perspective view from the front with the hose compartment 8 open, i.e. with the hose compartment lid 10 opened. According to FIG. 2, a hose or infusion hose 18 extends from the right, starting from an infusion container (not shown), into the hose compartment 8. The infusion hose 18 is not yet inserted as intended, but is shown in a raised position with respect to the operating state.

The hose compartment 8 has a hose inlet 20 in the area of a right side wall 22 from the operator's point of view, and a hose outlet 24 in the area of a left side wall 26.

The hose compartment lid 10, which is folded down as shown in FIG. 2, together with a base or bottom of the hose compartment 8 forms shaped sections, i.e. differently shaped sections adapted for contact with the infusion hose, into which the infusion hose 18 can be inserted in its operating state in a manner fixed to the housing. Closing the hose compartment lid 10 fixes the infusion hose 18 in this operating state.

With reference to the direction of conveyance from right to left according to FIGS. 1 and 2, a substantially rectangular recess 28 is provided in the housing 2 on the right side at the bottom of the hose compartment 8, in which an adapter portion 30 of the housing 2 is arranged. This recess 28 has a passage recess 32, rearward of which displacers 50 of a peristaltic displacement unit 46 are arranged, which will be explained in more detail in the following figures.

On both sides of the passage recess 32, in an extension direction of the infusion hose 18 when it is inserted into the hose pump 1 (i.e. in a longitudinal direction of the hose), a half-shell-shaped or half-cylindrical receptacle 34, 36 tapering in steps towards the passage recess 32 is provided for a coupling portion 38, 40 of the infusion hose 18. The passage recess 32 is spanned on the inside of the housing by a membrane 42, which separates an interior housing space of the infusion device 1 from the medical treatment space, or vice versa, protects the interior housing space against fluid, disinfectant or contamination penetrating from the outside.

According to FIG. 2, the coupling portions 38, 40 of the infusion hose 18 are insertable into the receptacles 34, 36, so that a hose portion or peristaltic portion 44 of the infusion hose 18 formed between the coupling portions 38, 40 is held in a linear/straight manner in the passage recess 32. The hose compartment lid 10 is closable by folding up. As a result, the infusion hose 18 is received in a form-fitting manner in the hose compartment 8 and clamped by the hose compartment lid 10 acting as a counter bearing. Displacers 50 of the hose pump (cf. following Figures) arranged behind the membrane 42 can then impress a peristaltic constriction of its cross-section on the infusion hose 18, or more precisely on the peristaltic portion 44 extending between the coupling portions 38, 40. As an alternative to the multi-piece hose/infusion hose 18 shown, the latter may be a single piece. In the first case, a specifically selected material of the hose portion to be loaded by the displacers, for example silicone, can be used to respond to mechanical requirements. The use of a one-piece hose, on the other hand, is simpler in terms of device technology.

Figure 3:
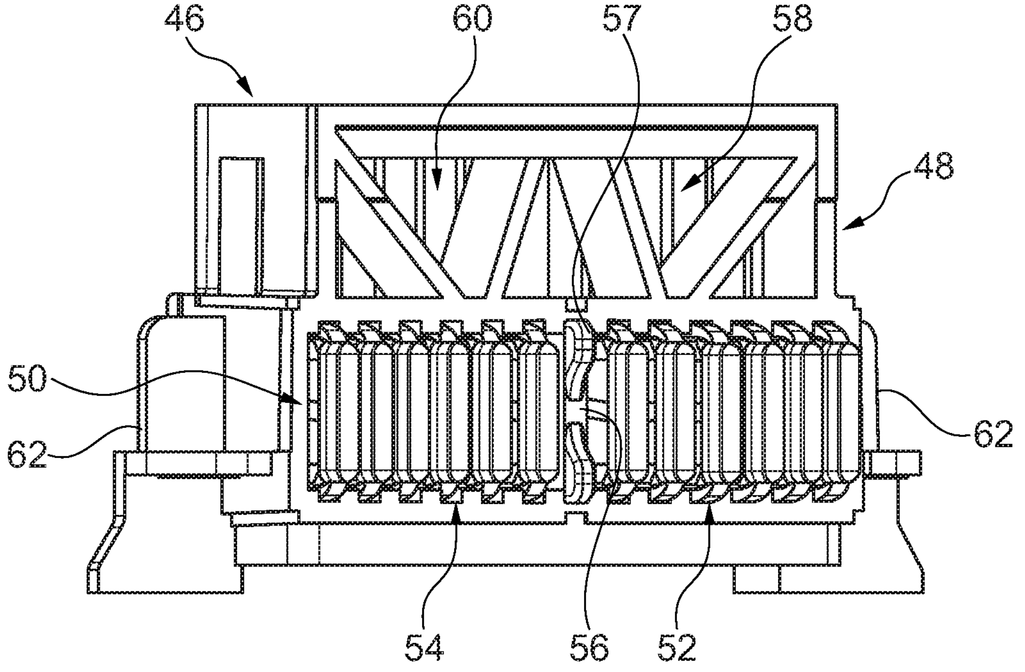
FIG. 3 shows a peristaltic displacement unit of the hose pump according to FIGS. 1 and 2 in a perspective view.

FIG. 3 shows the displacement unit 46 of the infusion device 1 already mentioned in the description of FIG. 2. The displacement unit 46 has a carrying structure 48 and displacers 50 accommodated therein so as to be linearly movable parallel to each other. These are flat and have conically tapering and rounded operating edges 51 facing the membrane 42 according to FIG. 2, which can be brought into contact with the membrane 42 and thus into operative engagement with the infusion hose 18 according to FIG. 2. The cross-section occupied by the operating edges 51 is somewhat smaller than that of the passage recess 32 according to FIG. 2. The displacers 50 are shown in more detail in FIG. 6, which shows each displacer having an operating edge 51, a rear edge 53, and a side edge 55 extending between the operating edge and the rear edge.

The carrying structure 48 is essentially cuboidal in shape. In the direction in which the infusion hose extends, i.e. from right to left in FIG. 3, two shafts 52 and 54 are provided side by side, in each of which six displacers 50 are arranged. The shafts 52, 54 are separated by a separation wall 56, from which a support element 57 protrudes, which in the case of a comparatively soft structure of the infusion hose 18 gives it a height guide. Above the two shafts 52, 54, an actuator space 58 is formed in the carrying structure 48, in which piezoelectric linear motors 60 are accommodated fixed to the housing. Each of the displacers 50 is coupled to one of the linear motors 60.

In the configuration example shown, the piezoelectric linear motors 60 are configured as stepper or walk-drive motor. Designs deviating from this are possible.

Fixing portions 62, via which the displacement unit 46 can be fixed in the housing 2 of the infusion device 1, project laterally from the carrying structure 48.

FIG. 3 clearly shows the comparatively small overall depth of the displacement unit 46. This is made possible by the fact that the displacers 50 are driven by linear motors according to the disclosure—and thus directly in their desired direction of actuation—so that there is no need for a gear device to convert a rotational movement of the displacers 50 into a linear movement.

Figure 4:
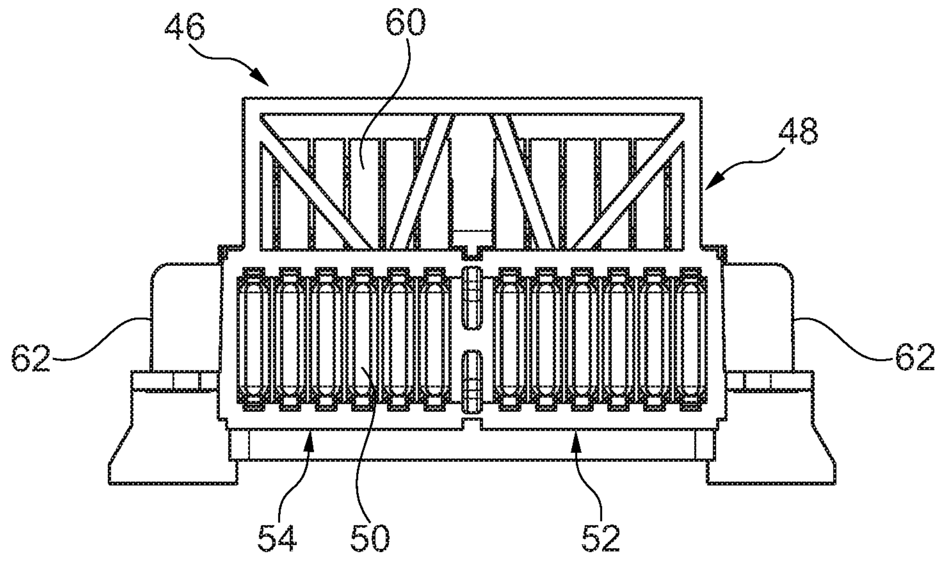
FIG. 4 shows a front view of the displacement unit according to FIG. 3.

FIG. 4 shows a front view of the displacement unit 46 according to FIG. 3, i.e. a front view of the hose compartment 8 according to FIG. 2 with the housing 2 removed. It can be clearly seen that the shafts 52, 54 each have an upper and a lower guide surface between which the displacers 50 are slidably mounted. Short guide lamellae or webs extend out of the guide surfaces, on or respectively between which the displacers 50 are laterally slidably guided.

Figure 5:
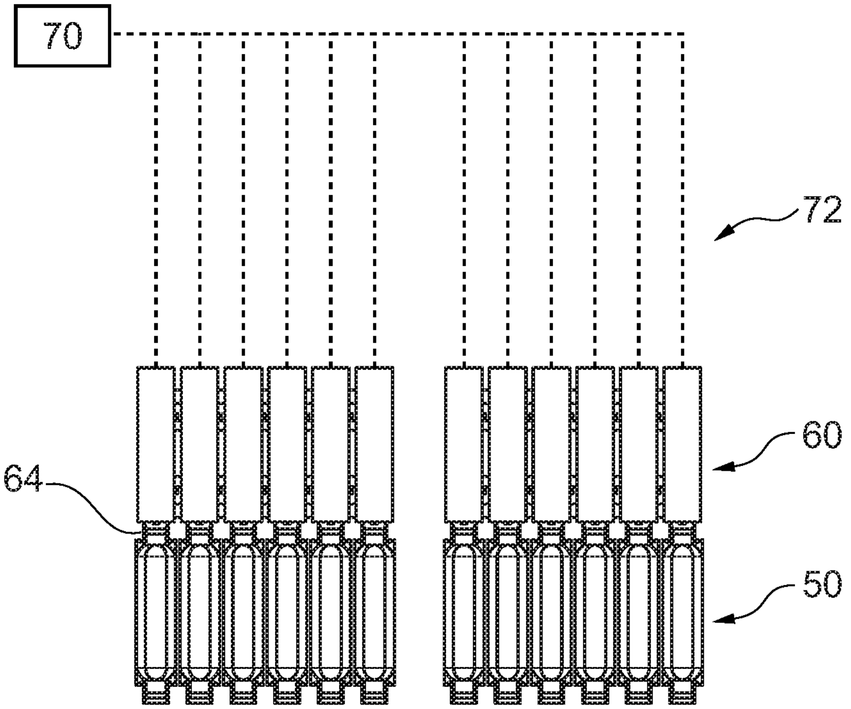
FIG. 5 shows a displacer of the displacement unit according to FIGS. 3 and 4, exposed in a front view.

FIG. 5 shows the units of displacers 50 and linear motors 60 exposed from the carrying structure 48 according to FIGS. 3 and 4, whereby a contact zone 64 of the respective linear motor 60 with its associated displacer 50 is visible.

Figure 6:
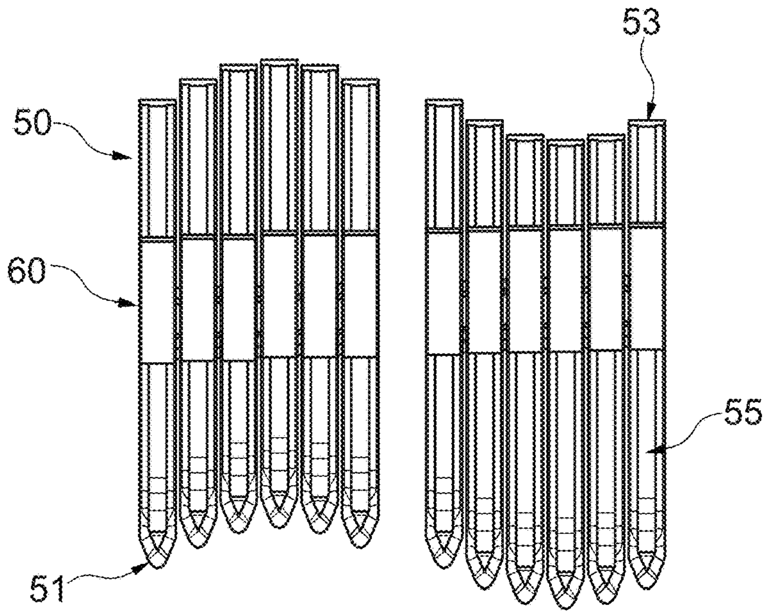
FIG. 6 shows the displacers according to FIG. 5 in a top view.

In order to generate the necessary peristaltic movement of the infusion hose 18, a roughly sinusoidal peristaltic movement pattern is alternately impressed on the displacers 50 via the linear motors 60 assigned to them in a predetermined sequence, which is shown at a time tin FIG. 6.

The hose pump 1 has a control unit 70 from which the linear motors 60 are drivable via signal line 72, in particular as a function of the parameters specified via the operator panel 6. The parameters stored in the control unit are a sequence of actuation of the displacer 50, its stroke, stroke speed and/or stroke force. These parameters can be changed using the buttons on the operator panel 6.

Figure 7:
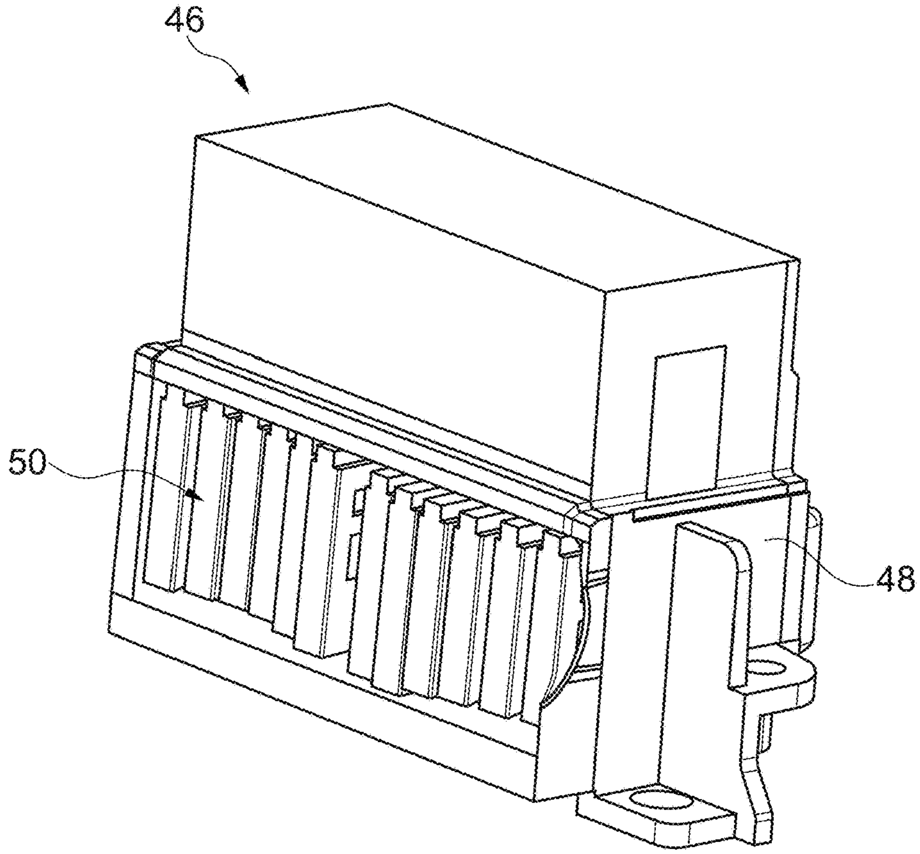
FIG. 7 shows the displacement unit according to FIG. 3, in a perspective view from behind.

FIG. 7 shows a perspective view of the displacement unit 46 from the rear, which again illustrates its comparatively small overall depth and the small installation space it occupies.

Figure 8:
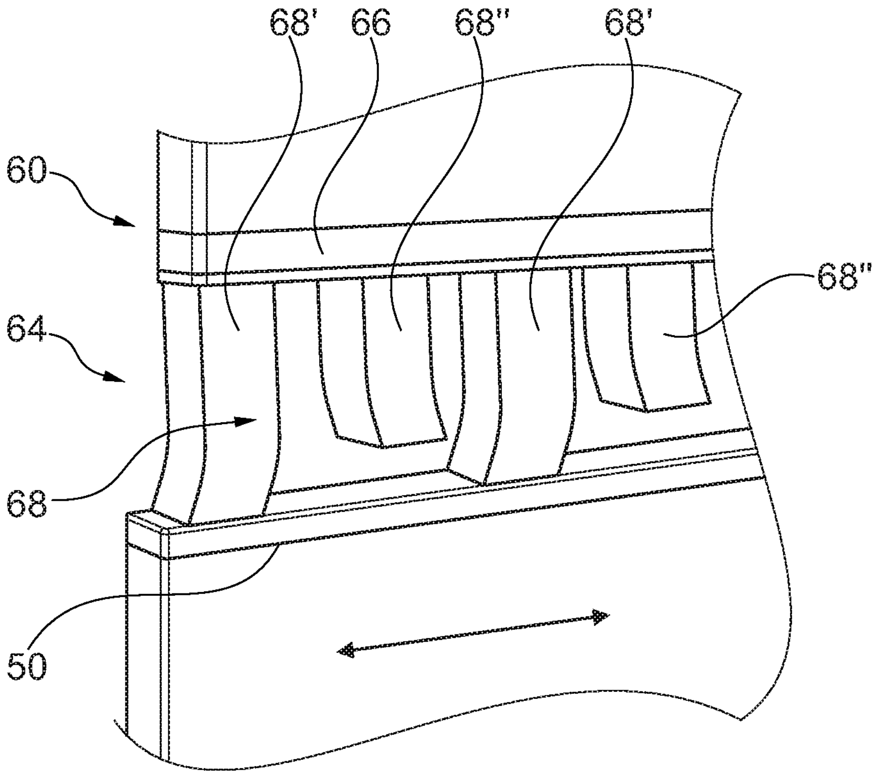
FIG. 8 shows a contact zone of one of the displacers with an associated linear motor according to FIGS. 3 to 7, in a detailed perspective view.

FIG. 8 shows in a schematic view a detailed view of the contact zone 64 between one of the displacers 50 and the piezoelectric linear motor 60 coupled to it. The latter is configured as a stepper motor and has a stator with a stator housing 66. For its driving and supply with electrical drive energy, the linear motor is electrically connected to the control unit of the hose pump via a contact lug (not shown). In the piezoelectric stepping motor embodiment, a plurality of bimorph bending actuators 68 project from the stator housing 66 and are deformable in and against the direction of actuation of the displacer 50 (along the double arrow) and are liftable transversely thereto. In the present example, the bending actuators 68 are deformable in such a way that their free ends, which are configured for frictional contact with the displacer 50, can be folded through a certain angle depending on energization of the bending actuators 68.

In addition to the linear motors 60 shown in FIG. 8, which are arranged on only one upper side of the displacer 50, they can of course also be arranged on an additional side of the displacer 50, for example its underside. The arrangement may be a mirror image.

At the time shown in FIG. 8, the direction of actuation towards the infusion hose is assumed to be from left to right. By applying the appropriate energization, two bending actuators 68" are lifted off and two other bending actuators 68' are deformed with the maximum possible return stroke (i.e. a maximum position set back against the direction of actuation), against the direction of actuation, and are placed on the displacer 50.

When the driving is changed, the latter two bending actuators 68' remain seated on the displacer 50 and are deformed to the right in FIG. 8 in this way, i.e. brought into a maximum possible pre-stroke. This causes a linear movement of the displacer 50 in FIG. 8 to the right, towards the infusion hose 18, via the frictional force transmitted to the displacer 50.

Once they have reached their maximum possible stroke in the actuating direction (pre-stroke), the two bending actuators 68' remain seated and the other two 68" are deformed in the lifted position to their maximum possible return stroke, against the actuating direction, and are then seated.

In this state, all bending actuators 68' and 68" are briefly seated, the first-mentioned bending actuators 68' with maximum possible stroke in the actuating direction, the other bending actuators 68" with maximum possible stroke against the actuating direction. In this way, the displacer 50 is 'transferred' from one bending actuator 68' to the other bending actuators 68".

The one bending actuators 68' are lifted off and deformed against the direction of actuation from right to left, and the other bending actuators 68" are deformed in the direction of actuation from left to right.

The described driving is performed for all linear motors 60 in a sequence stored in the control unit for execution depending on at least one of the parameters of stroke, stroke speed and stroke force. In particular, the control unit is configured to determine the parameters from a volume flow specified by the operator.

The described use of the piezoelectric linear motors 60 makes it possible to implement the principle of displacers 50 arranged side by side, which perform a peristaltic movement or respectively imprint it on the infusion hose 18. The respective bending actuators 68 of the respective piezoelectric linear motor 60 'run' on the associated displacer 50 and move it back and forth in the direction of actuation, depending on the time-related driving via the control unit.

A significant advantage of the design of the displacement unit 46 described is its reliability and durability. The design of the piezoelectric linear motor 60 based on crystalline structures is subject to little or no significant wear. A space requirement of the linear motor 60, in particular its overall installation height and/or width, is small, and its controllability has high-resolution and may be, for example, in the nanometer range. In this way, the position of the displacer 50 relative to the (infusion) hose 18 can be controlled in the nanometer range. As a result, the force exerted by the displacer 50 on the hose 18, and consequently the pressure in the hose 18, can also be influenced extremely precisely. The achievable speeds are also high. For example, linear movements at 500 mm/sec are possible. In principle, one advantage of this design is a low energy requirement due to fewer components and friction. Since fewer components are required for the same function as in the prior art, this also results in a smaller installation space required as well as a lower weight, both of the displacement unit 46 and of the hose pump 1 in which the displacement unit 46 is inserted. Another advantage is a lower assembly effort resulting from the reduced number of components.

In summary, disclosed is a peristaltic displacement unit for a medical hose pump having a plurality of linear motors for generating a peristaltic motion of a fluid-carrying hose so that the hose is kneaded in an intended direction and thus conveys the fluid.

The invention claimed is:

1. A displacement unit for a medical hose pump with linearly movable actuatable plungers, which are actuatable with a predetermined sequence by a drive device of the displacement unit for generating a peristaltic movement of a hose or hose portion transversely to the hose or hose portion and against the hose or hose portion in order to squeeze the hose or hose portion, wherein the drive device has linear motors, each of which is coupled to one of the plungers, and at least one of the linear motors being a piezoelectric linear motor, each plunger comprising an operating edge configured to face the hose or hose portion, a rear edge opposite the operating edge, and a side edge extending between the operating edge and the rear edge, each linear motor configured to apply a pre-stroke force to the side edge of the respective plunger to displace the operating edge toward the hose or hose portion, and each linear motor configured to apply a return stroke force to the side edge of the respective plunger to displace the operating edge away from the hose or hose portion.

2. The displacement unit according to claim 1, wherein the medical hose pump is an infusion device or an infusion pump or a hose pump for medical dosage or for extracorporeal blood treatment.

3. The displacement unit according to claim 1, wherein at least one of the linear motors is a piezoelectric stepper motor.

4. The displacement unit according to claim 1, wherein the linear motors are arranged and movable parallel to each other.

5. The displacement unit according to claim 1, wherein the linear motors are each arranged laterally to the plungers with respect to a direction of movement of the plungers.

6. The displacement unit according to claim 1, wherein each side edge is configured for friction fit and/or form fit with at least one flexible actuator of the linear motors.

7. The displacement unit according to claim 6, wherein the at least one flexible actuator of the linear motors is an amorphous bending actuator.

8. The displacement unit according to claim 6, wherein each side edge is flat.

9. The displacement unit according to claim 6, further comprising a housing in or on which the plungers are mounted linearly movably, wherein at least one lateral rim of the plungers is configured as at least one guide rail which is guided longitudinally movable in or on the housing.

10. The displacement unit according to claim 9, wherein the at least one lateral rim of the plungers is adjacent to a respective side edge.

11. The displacement unit according to claim 9, wherein the housing forms at least one shaft in which the plungers are mounted in a linearly moveable manner and are spaced apart from each other.

12. The displacement unit according to claim 1, comprising a control unit via which a stroke or a force of at least one of the plungers can be controlled or regulated.

13. The displacement unit according to claim 1, comprising a housing in or on which the plungers are mounted linearly movable, and in which stators of the linear motors are housed.

14. A medical hose pump comprising:

the displacement unit according to claim 1; and a housing with an externally accessible passage recess, into or via which a fluid-carrying or blood-carrying hose or hose portion is insertable or spannable, the displacement unit being accommodated in the housing, the plungers configured to operatively engage the hose or hose portion through the passage recess or in the region of the passage recess in order to generate a peristaltic movement of the hose or hose portion.

* * * * *